United States Patent [19]

Sano et al.

[11] Patent Number: 6,156,796
[45] Date of Patent: Dec. 5, 2000

[54] AGRICULTURAL/HORTICULTURAL FUNGICIDAL COMPOSITIONS

[75] Inventors: Shinsuke Sano, Kanagawa; Homare Yamanaka, Shizuoka, both of Japan

[73] Assignee: Nippon Soda Co., Ltd., Tokyo, Japan

[21] Appl. No.: 09/147,343

[22] PCT Filed: Jun. 3, 1997

[86] PCT No.: PCT/JP97/01880

§ 371 Date: Dec. 4, 1998

§ 102(e) Date: Dec. 4, 1998

[87] PCT Pub. No.: WO97/46097

PCT Pub. Date: Dec. 11, 1997

[30] Foreign Application Priority Data

Jun. 4, 1996 [JP] Japan ................................. 8-163743

[51] Int. Cl.$^7$ .......................... A01N 37/12; A01N 37/18; A01N 37/44; A01N 43/54; A01N 43/40
[52] U.S. Cl. .......................... 514/539; 514/255; 514/269; 514/335; 514/364; 514/415; 514/423; 514/427; 514/452; 514/523; 514/532; 514/538; 514/616; 514/617; 514/619
[58] Field of Search ........................... 514/617, 523, 514/538, 539, 616, 427, 423, 255, 532, 452, 619, 335, 364, 415, 269

[56] References Cited

U.S. PATENT DOCUMENTS 5,847,005 12/1998 Kasahara et al. ..................... 514/617
5,942,538 8/1999 Kasahara et al. ..................... 514/427

FOREIGN PATENT DOCUMENTS

WO96/19422 6/1996 WIPO .

OTHER PUBLICATIONS

Tomlin, The Pesticide Manual Incorporation The Agrochemicals Handbook, 10 Edition (1995), p. 579.

*Primary Examiner*—Allen J. Robinson
*Attorney, Agent, or Firm*—Jacobson, Price, Holman & Stern, PLLC

[57] ABSTRACT

The present invention is directed to fungicidal compositions for agricultural and horticultural use, characterized in that the composition comprises a benzamidoxime composed represented by a general formula [I]:

[I]

wherein $R^1$ represents alkyl, alkenyl, etc., $R^2$ represents phenyl, heterocycle, etc., $X^1$ represents haloalkyl, $X^2$, $X^3$, $X^4$ and $X^5$ each independently represent hydrogen, halogeno, alkyl, etc., $r_1$ and $r_2$ each independently represent hydrogen, halogeno, alkyl, etc., and a so-called acrylate fungicide as the active ingredients. The fungicidal compositions according to the present invention are combination compositions of fungicidal components, which can improve fungicidal activity obtainable with each component in the combination with a less dose in total of each components.

4 Claims, No Drawings

AGRICULTURAL/HORTICULTURAL FUNGICIDAL COMPOSITIONS

This application is a 371 of PCT/JP97/01880, filed Jun. 3, 1997.

FIELD OF THE INVENTION

The present invention is directed to fungicidal compositions, particularly to fungicidal compositions suitable to control powdery mildew disease growing on various agricultural and horticultural crops.

1. Background Art

Benzamidoxine derivatives represented by a general formula [I]:

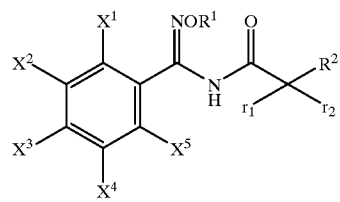

[I]

are the compounds which have fungicidal activity and are disclosed in WO 96/19442 Gazette filed by the inventors of the present invention.

Whereas, so-called acrylate fungicides, for example, ICIA 5504, BASF 490, SSF-126, etc. have been known as new type fungicides for agricultural and horizontal use (see EP 477631, EP 253213 and EP 38237 Gazettes).

However, fungicidal compositions comprising a compound represented by a general formula [I] and an acrylate fungicide and capable of providing synergistic activity have not been known yet.

2. Disclosure of the Invention

It is an object of the present invention to lower the effective dose of the compounds known as having fungicidal activity against plant diseases, to improve their activity spectrum as a fungicide, and to provide fungicidal compositions in combination which can work with the active ingredients at a less dose in total and improve the effective control value with providing synergistic activity.

The present invention is directed to fungicidal compositions characterized in that each compositions comprises a benzamidoxime compound A represented by a general formula [I]:

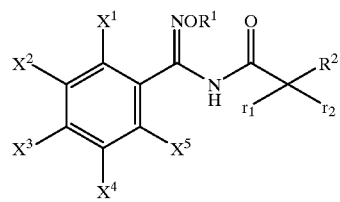

[I]

wherein $R^1$ represents optionally-substituted C1–C4 alkyl, optionally-substituted C2–C4 alkenyl or optionally-substituted C2–C4 alkynyl, $R^2$ represents optionally-substituted phenyl or optionally-substituted heterocycle.

$X^1$ represents C1–C4 haloalkyl, $X^2$, $X^3$, $X^4$ and $X^5$ each independently represent hydrogen, halogeno, C1–C4 alkyl, C1–C4 haloalkyl, C1–C4 alkoxy, C1–C4 haloalkoxy, C1–C4 alkylthio, C1–C4 alkylsulfinyl, C1–C4 alkylsulfonyl, nitro, amino or C1–C4 alkylcarbonylamino.

$r^1$ and $r^2$ each independently represent hydrogen, halogeno, C1–C4 alkyl, C1–C4 haloalkyl, C1–C4 alkoxy, C1–C4 alkylthio or amino, or, $r^1$ and $r^2$ may get together to form carbonyl, and one or more than 2 compounds selected from a group B consisting of the compounds (a) through (n) as shown below as the active ingredients thereof.

B:

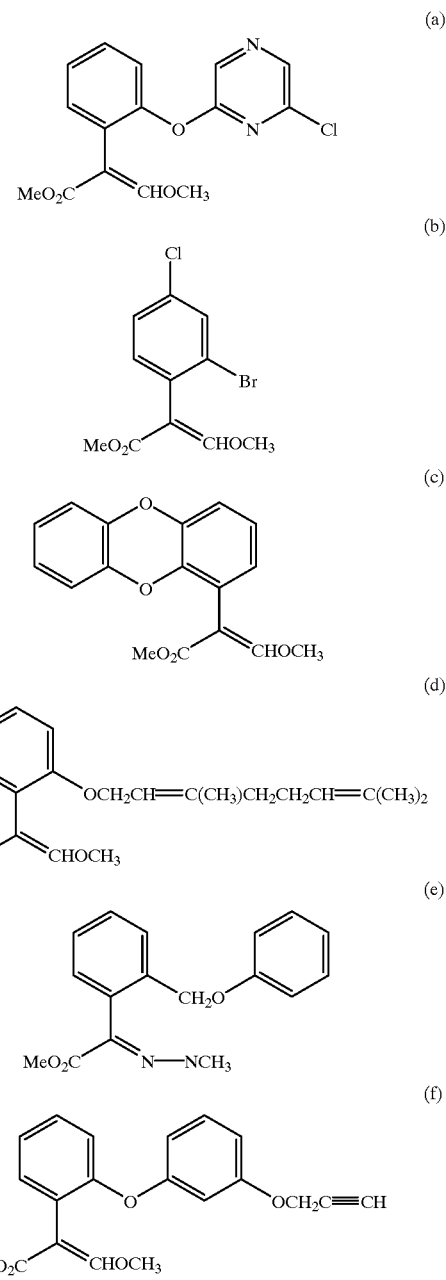

-continued (g)
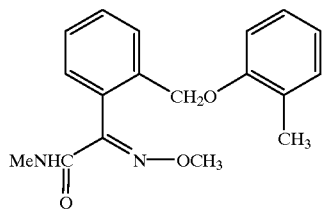

(h)
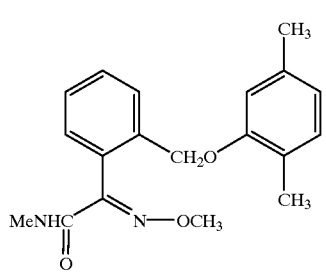

(i)
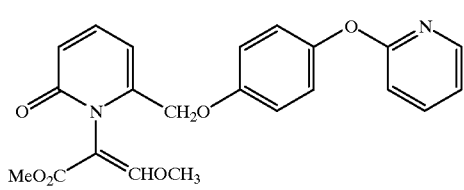

(j)
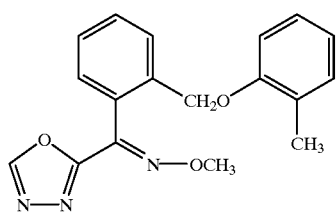

(k)
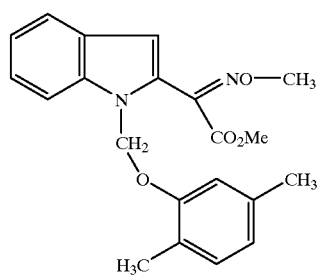

(l)
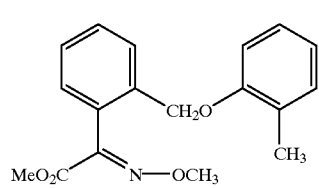

-continued (m)
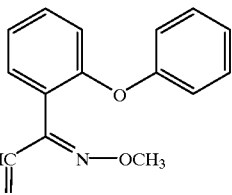

(n)
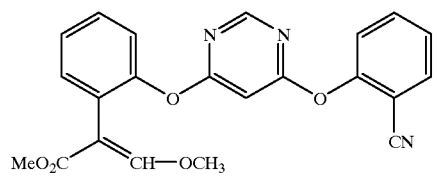

The benzamidoxime compounds to be used in the present invention are the compounds represented by the general formula [I] as described above, and one or more than 2 of the compounds can be used as the active ingredient for the fungicidal compositions specified in the present invention.

Preferable examples for the benzamidoxime compounds represented by a general formula [I] are shown in Table 1.

TABLE 1

($r_1, r_2 = H$)

| No. | $X_2$ | $X_3$ | $X_4$ | $X_5$ | $R_1$ | $R_2$ |
|-----|-------|-------|-------|-------|-------|-------|
| 1 | H | H | F | F | $CH_2$—cyclopropyl | Ph |
| 2 | H | H | Cl | F | $CH_2$—cyclopropyl | Ph |
| 3 | H | H | F | Cl | $CH_2$—cyclopropyl | Ph |
| 4 | H | H | Cl | Cl | $CH_2$—cyclopropyl | Ph |
| 5 | H | H | F | F | $CH_2$—cyclopropyl | 2-F—Ph |
| 6 | H | H | Cl | F | $CH_2$—cyclopropyl | 2-F—Ph |
| 7 | H | H | F | Cl | $CH_2$—cyclopropyl | 2-F—Ph |
| 8 | H | H | Cl | Cl | $CH_2$—cyclopropyl | 2-F—Ph |

TABLE 1-continued

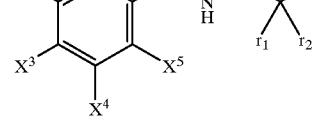

(r₁, r₂ = H)

| No. | X₂ | X₃ | X₄ | X₅ | R₁ | R₂ |
|---|---|---|---|---|---|---|
| 9 | H | H | F | F | CH₂-cyclopropyl | 2-F-5-Me—Ph |
| 10 | H | H | Cl | F | CH₂-cyclopropyl | 2-F-5-Me—Ph |
| 11 | H | H | F | Cl | CH₂-cyclopropyl | 2-F-5-Me—Ph |
| 12 | H | H | Cl | Cl | CH₂-cyclopropyl | 2-F-5-Me—Ph |
| 13 | H | H | F | F | CH₂CH₂Cl | Ph |
| 14 | H | H | Cl | F | CH₂CH₂Cl | Ph |
| 15 | H | H | F | Cl | CH₂CH₂Cl | Ph |
| 16 | H | H | Cl | Cl | CH₂CH₂Cl | Ph |
| 17 | H | H | F | F | CH₂CH₂Cl | 2-F—Ph |
| 18 | H | H | Cl | F | CH₂CH₂Cl | 2-F—Ph |
| 19 | H | H | F | Cl | CH₂CH₂Cl | 2-F—Ph |
| 20 | H | H | Cl | Cl | CH₂CH₂Cl | 2-F—Ph |
| 21 | H | H | F | F | CH₂CH₂Cl | 2-F-5-Me—Ph |
| 22 | H | H | Cl | F | CH₂CH₂Cl | 2-F-5-Me—Ph |
| 23 | H | H | F | Cl | CH₂CH₂Cl | 2-F-5-Me—Ph |
| 24 | H | H | Cl | Cl | CH₂CH₂Cl | 2-F-5-Me—Ph |

In the present invention, the acrylate fungicides are defined as fungicidal substances which have been developed from natural substances, such as Oudemansin A and Strohilurine A, as a leading compound and contain any of alkoxymethylene group, alkoxyimino group or the like in the part of their molecular structures.

As examples for the acrylate fungicides as specified in the present invention, compounds (a) through (n) as described above can be preferably given. Considering C=X double bond contained in the acrylate fungicides, both E-type constitutional isomer and Z-type constitutional isomer can work as regard to the performance against carboxylates. Therefore, in case of the mixed compositions according to the present invention, any of purely E-type constitutional isomer, purely Z-type constitutional isomer and racemic mixture thereof can be used as a fungicide.

In the fungicidal compositions according to the present invention, a mixing ratio for a compound A represented by a general formula [I] and an acrylate compound B can be flexibly changed over a wide range, however, it is normally in a range of 1:0.01–1,000 on weight basis, and more preferably in a range of 1:100.

Further, the fungicidal compositions according to the present invention can be prepared into a formulation, such as oil solution, emulsifiable concentrate, wettable powder, granules, powder, aerozol, suspension concentrate, flowable concentrate, microcapsules, ULV, paste etc. by mixing normally with solid carrier, liquid carrier, or gasificated carrier, and with a surfactant or other adjuvant for formulation, if appropriate. In the formulations described above, the active ingredients described above are preferably contained at a total rate of 0.1 to 99.9% by weight, and more preferably at a total rate of 0.2 to 80% by weight.

As examples for a solid carrier to be used for the preparations of formulations, clay, such as kaolinite, diatomaceous earth, synthesized silicon oxide hydrate, fubasami clay, bentonite and acid clay, talc, fine powder or granules of other inorganic minerals, such as sericite, silica powder, sulfur powder, activated carbon and potassium carbonate, can be given. As examples for a liquid carrier to be used for the same, water, alcohols, such as methanol and ethanol, ketones, such as acetone, methyl ethyl ketone and cyclohexanone, aromatic hydrocarbons, such as toluene, xylene, ethyl benzene and methyl naphthalene, nonaromatic hydrocarbons, such as hexane, cyclohexane and kerosine, esters, such as ethyl acetate and butyl acetate, nitriles, acetinitrile and isobutylonitrile, ethers, dioxane and diisopropylether, acid amides, such as dimethylformamide and dimethylacetoamide, and halogenated hydrocarbons, such as dichloroethane and trichloroethane, can be given. As examples for a gas carrier, namely an injecting agent, carbon dioxide, butane gas, fluorocarbon, etc., can be given.

As examples for a surface active agent, alkylsulfate esters, alkylsulfates, alkylarylethers and their polyoxyethylenes, polyethyleneglycols, polyhydric alcohol esters, and sugar alcohol derivatives can be given. As examples for other inactive ingredients for formulation, a sticking agent and a dispersant, such as casein, gelatin, polysaccharides including starch, gum arabic, cellulose derivatives and alginic acid, lignin derivatives, bentonite and synthetic aqueous polymers including polyvinyl alcohol, polyvinyl pyrrolidone and polyacrylic acid, and a stabilizer, such as PAP (acidic isopropyl phosphate), BHT (2,6-di-tert-butyl-4-methylphenol), BHA (2-/3-tert-butyl-4-methoxyphenol), vegetable oils, mineral oils, fatty acids and fatty acid esters, can be given.

The formulated fungicidal compositions according to the present invention can be applied either directly or following to dilution with water, etc. onto plants, water surface and soil. Furthermore, the inventive fungicidal compositions can be used in combination with any of other fungicides, insecticides, herbicides, fertilizers, soil reforming agents, etc. The dose of the fungicidal composition according to the present invention to be applied shall be variable depending upon each of a combination ratio of an active compound represented by a general formula [I] and a so-called acrylate fungicide, climatic condition, formulation type, time to apply, method to apply, place to apply, objective pest diseases, objective crops, etc., however, it is normally in a range of from 1 to 1,000 g as active component per ha, and more preferably in a range of from 10 to 100 g as the active components per ha. Whereas, the concentration of the fungicidal composition of the present invention preferably be applied, in case that the composition is formulated into any of emulsifiable concentrate, wettable powder, suspension concentrate and liquid and is applied following to dilution with water, it is normally in a range of from 1 to 1,000 ppm, and more preferably in a range of from 10 to 250 ppm, in case that the fungicidal compositions of the present invention are formulated into either granules or powder, it should be applied directly without preparing the diluted solution thereof.

BEST MODE FOR CARRYING OUT THE INVENTION (Examples)

Now, the usefulness of the compositions of the present invention as a fungicide for controlling powdery mildew disease attacking various agricultural and horticultural crops is demonstrated with referring to the following Test Examples. The fungicidal activity of the compositions were evaluated by conducting a macroscopic observation on degrees of symptom of powdery mildew disease appeared on plant leaves at the time assessment and comparing such symptoms of leaves with the one in plots for no-treatment. Whereas, for comparison purpose, a conventional emulsifiable concentrate formulation of the composition of the present invention was prepared by admixing compound A represented by a general formula [I] (Compound No. 1 in Table 1) and an acrylate fungicide B at a predetermined ratio.

Test Example 1: Test for controlling powdery mildew disease on wheat plants.

Emulsion prepared with the conventional emulsifiable concentrate formulated for the composition of the present invention to a predetermined concentration was sprayed onto young seedlings leaves of wheat plants (variety: Chihoku, 1–1.5 leaf stage) grown in a clay pot. After naturally drying the leaves at room temperature, the leaves were inoculated with the spores of Erysiphe graminis f. sp. tritici and were subjected to the infection for 7 days in a chamber maintained at approximately 22° C. The degree of symptoms caused by powdery mildew disease on the leaves were compared with the ones on leaves in the no-treatment plots to evaluate the preventing effectiveness of the composition. The results are shown in Table 2.

The effective degree E of the compositions of the present invention are calculated according to Corby's formula (Weed., 15, 20–22, 1966) and is compared with the results, respectively.

$$E = x + y - \frac{x \cdot y}{100}$$

E is a value in percent as an expected effective degree when active compounds A and B were used at a concentration of m and n, respectively. X is a value in percent as an expected effective degree when active compound A was used at a concentration of m, whereas y is a value in percent as an expected effective degree when active compound B was used at a concentration of n.

TABLE 2

| Active Substance | Concentration of Active Substance in Spray Solution (ppm) | Actual Effective Degree (%) | Calculated Effective Degree (%) |
| --- | --- | --- | --- |
| Water (No treatment) | 0 | 0 | — |
| Compound A in WO96/19442 (No. 1) | 0.2 | 13 | — |
| | 0.05 | 0 | — |
| Known Substance (1) | 0.05 | 38 | — |
| | 0.0125 | 19 | — |
| A + B | 0.2 + 0.05 | 81 | 41 |
| | 0.2 + 0.0125 | 30 | 30 |
| | 0.05 + 0.05 | 38 | 38 |

From the results as described above, it is understandable that the actual effective degree is more improved than the effective degree calculated according to Corby's formula.

Industrial Use of the Invention

It is an object of the present invention to provide fungicidal compositions which can excellently control plant diseases growing on various agricultural and horticultural crops, powder mildew disease, in particular.

What is claimed is:

1. A fungicidal composition comprising synergistic fungicidally effective amounts of a benzamidoxime compound having a formula I:

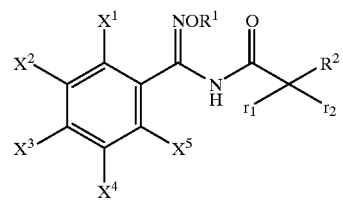

wherein $R^1$ represents optionally-substituted $C_1$–$C_4$ alkyl or optionally-substituted $C_2$–$C_4$ alkenyl, $R^2$ represents optionally-substituted phenyl or an optionally-substituted heterocyclic moiety, $X^1$ represents $C_1$–$C_4$ haloalkyl, $X^2$, $X^3$, $X_4$ and $X^5$ each independently represent hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, nitro, amino or $C_1$–$C_4$ alkyklcarbonylamino, $r_1$ and $r_2$ each independently represent hydrogen, halogen, $C_1$–$C_4$ alkyl, $C_1$–$C_4$ haloalkyl, $C_1$–$C_4$ alkoxy, $C_1$–$C_4$ alkylthio or amino, or $r_1$ and $r_2$ may together form carbonyl, and one or more compounds selected from the group consisting of compounds (a) through (n) as an active ingredient:

(a)

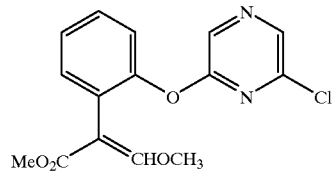

(b)

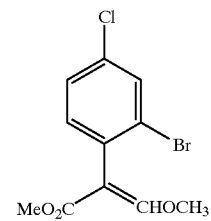

(c)

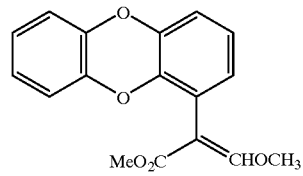

(d)

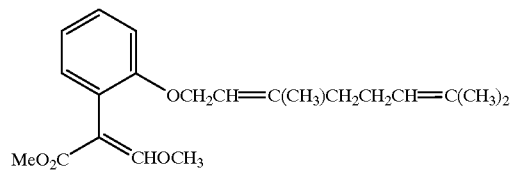

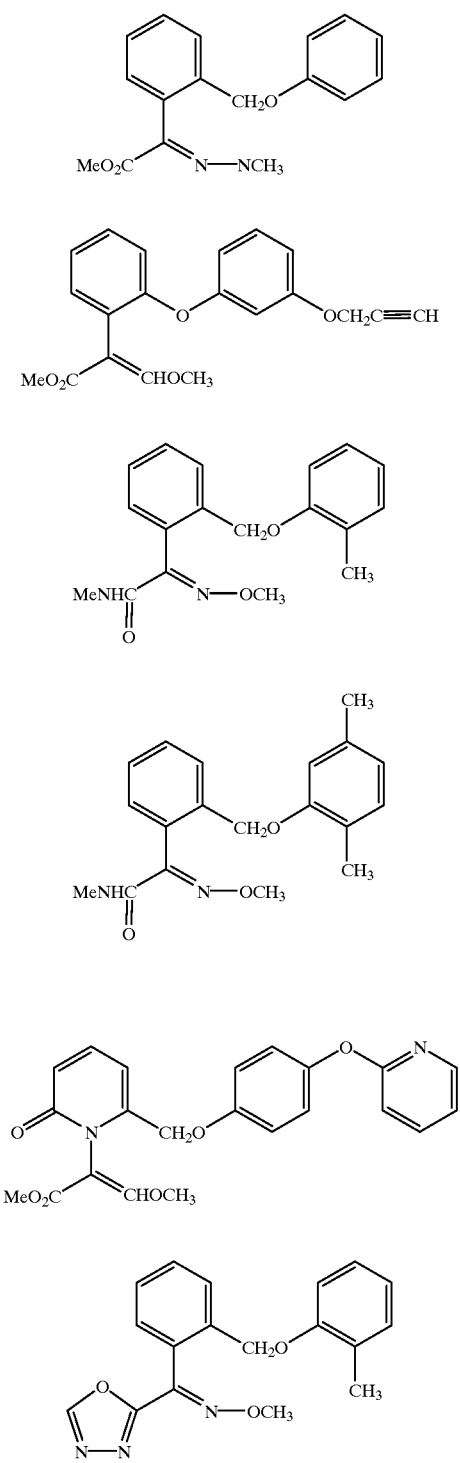

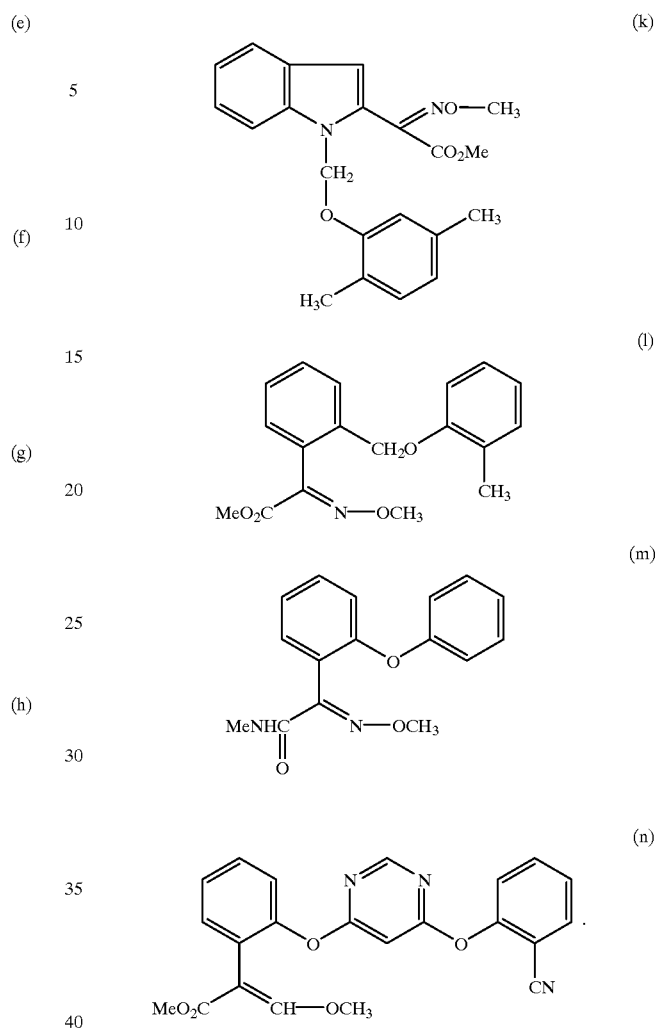

2. The fungicidal composition according to claim 1, wherein $R^1$ is cyclopropyl methyl or 2-chloroethyl, $R^2$ is phenyl optionally substituted by halogen or methyl, $X^1$ is $CF_3$, $X^2$ and $X^3$ are each hydrogen, $X^4$ and $X^5$ are each halogen and $r_1$ and $r_2$ are each hydrogen.

3. The fungicidal composition according to claim 1, wherein $R^1$ is cyclopropyl methyl, $R^2$ is phenyl, $X^1$ is $CF_3$, $X^2$ and $X^3$ are each hydrogen, $X^4$ and $X^5$ are each fluorine and $r_1$ and $r_2$ are each hydrogen.

4. The fungicidal composition according to claim 3, wherein the one or more compounds selected from the group consistion of compounds (a) through (n) is compound (l).

* * * * *